United States Patent [19]
Lee et al.

[11] Patent Number: 5,633,552
[45] Date of Patent: May 27, 1997

[54] CANTILEVER PRESSURE TRANSDUCER

[75] Inventors: Seung S. Lee, Richmond; Richard M. White; Albert P. Pisano, both of Berkeley, all of Calif.

[73] Assignee: The Regents of the University of California, Oakland, Calif.

[21] Appl. No.: 258,046

[22] Filed: Jun. 10, 1994

Related U.S. Application Data

[63] Continuation-in-part of Ser. No. 72,294, Jun. 4, 1993, abandoned.

[51] Int. Cl.$^6$ ................................ H01L 41/08
[52] U.S. Cl. ..................... 310/311; 310/332; 310/328
[58] Field of Search .......................... 310/309, 311, 310/328, 331, 332; 29/25.35

[56] References Cited

U.S. PATENT DOCUMENTS

| | | | |
|---|---|---|---|
| 4,783,821 | 11/1988 | Muller et al. | 381/173 |
| 5,001,993 | 3/1991 | Brand | 73/651 |
| 5,006,749 | 4/1991 | White | 310/323 |
| 5,025,346 | 6/1991 | Tang et al. | 361/83 |
| 5,049,775 | 9/1991 | Smits | 310/328 |
| 5,072,288 | 12/1991 | MacDonald | 310/332 |
| 5,129,262 | 7/1992 | White et al. | 73/599 |
| 5,138,216 | 8/1992 | Woodruff et al. | 310/332 |
| 5,162,691 | 11/1992 | Mariani et al. | 310/331 |
| 5,248,912 | 9/1993 | Zdeblick et al. | 310/332 |
| 5,260,596 | 11/1993 | Dunn et al. | 257/414 |
| 5,339,289 | 8/1994 | Erickson | 367/149 |
| 5,366,587 | 11/1994 | Ueda et al. | 310/309 |
| 5,396,066 | 3/1995 | Ikeda et al. | 310/309 |
| 5,418,771 | 5/1995 | Kasanuki et al. | 369/126 |

FOREIGN PATENT DOCUMENTS

| | | | |
|---|---|---|---|
| 4-186784 | 7/1992 | Japan | 310/311 |

OTHER PUBLICATIONS

Kim, E.S. et al., "Improved ICI–compatible piezoelectric Microphone and CMOS process," *Transducers*, 1991, San Francisco.

Kim, E.S. et al., "IC–processed Piezoelectric Microphone," *IEEE Electron Device Lett.*, vol EDL–8, Oct. 1987, pp. 467–468.

Donk, et al., "Preliminary results of a silicon condenser microphone with internal feedback," *Transducers*, 1991, San Francisco.

(List continued on next page.)

*Primary Examiner*—Thomas M. Dougherty
*Attorney, Agent, or Firm*—Fish & Richardson, P.C.

[57] ABSTRACT

Micromachined cantilever pressure transducers, which work both as microphones and as microspeakers, are disclosed. These devices are made possible by novel methods for producing flat, thin film multilayer or polymeric cantilevers.

29 Claims, 13 Drawing Sheets

OTHER PUBLICATIONS

Bearden, et al., *Optics Lett.*, vol. 18, No. 3, Feb. '93, pp. 238–240.

Junger, et al., *Sound Structures and Their Interaction*, pp. 235–272, MIT Press, 1986.

Kaliski, S., et al., *Vibrations and Waves*, 1992, pp. 313–325.

G.M. Sessler, "Acoustic Sensors," *Sensors and Actuators*, A25–A27, pp. 323–330, 1991.

J. Bergqvist et al., "A New Condenser Microphone in Silicon," *Sensors and Actuators*, A21–A23, pp. 123–125, 1990.

W. Kuhnel et al., "Micromachined Subminiature Condenser Microphones in Silicon," *Sensors and Actuators*, A32, pp. 560–564, 1992.

R.P. Ried, et al., "Residual–Stress Compensation in Clamped–Clamped Micromachined Plates," *Micromechanical Systems, ASME Winter Annual Mtg.*, Anaheim, California, pp. 23–32, Nov. 1992.

E. Graf et al., "Silicon Membrane Condenser Microphone with Integrated Field–Effect Transistor," *Sensors and Actuators*, A37–A38, pp. 708–711, 1993.

T. Bourouina et al., "A New Condenser Microphone with a p+ Silicon Membrane," *Sensors and Actuators*, A31, pp. 149–152, 1992.

E.S. Kim, "Integrated Microphone with CMOS Circuits on a Single Chip," *Ph.D. Thesis*, EECS Dept., University of California at Berkeley, May 1990, pp. 141–145, 152–164.

P. Krulevitch et al., "Stress and Microstructure in Phosphorus Doped Polycrystalline Silicon," *Mat. Res. Soc. Symp. Proc.*, vol. 276, pp. 79–84, 1991.

M. Sekimoto et al., "Silicon Nitride Single–layer X–ray Mask," *J. Vac. Sci. Technol.*, vol. 21(4), pp. 1017–1021, 1982.

H.C. Nathanson et al., "The Resonant Gate Transistor," *IEEE Trans. Electron Devices*, vol. ED–14, No. 3, Mar. 1967, pp. 117–133.

G.C. Johnson et al., "Stress Gradients in Thin Films Used in Micro–Electro–Mechanical Systems," *Proceedings of the Mini–Symposium on Microelectromechanical Systems* to be held at ASME Winter Annual Meeting, New Orleans, Nov. 1993.

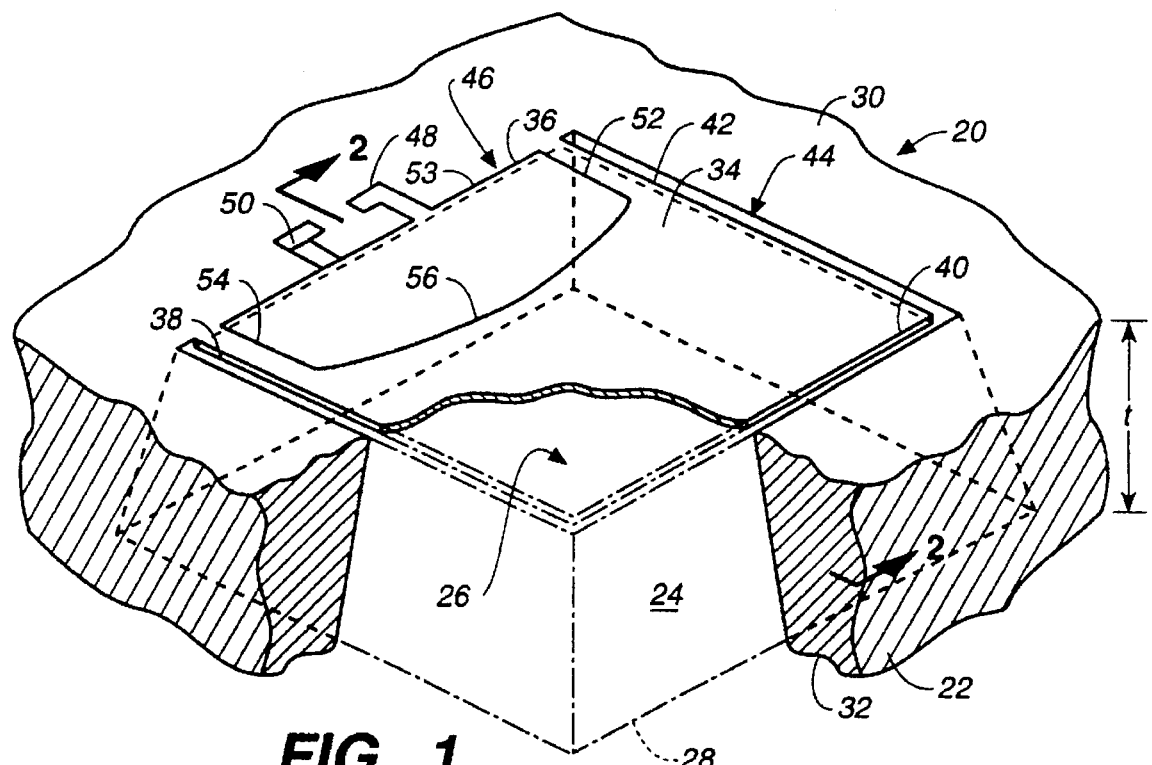
FIG._1
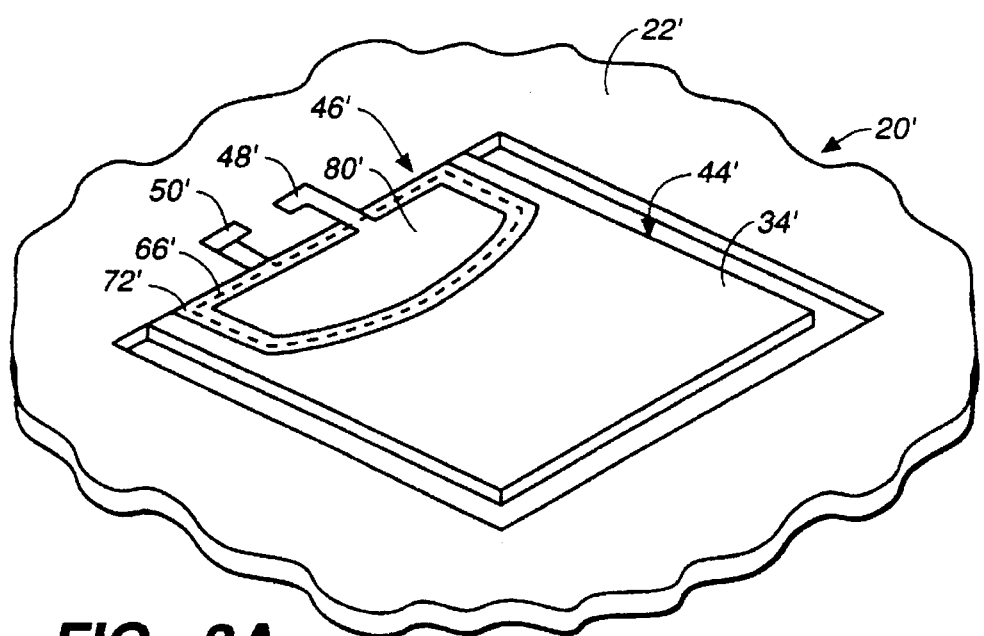
FIG._3A

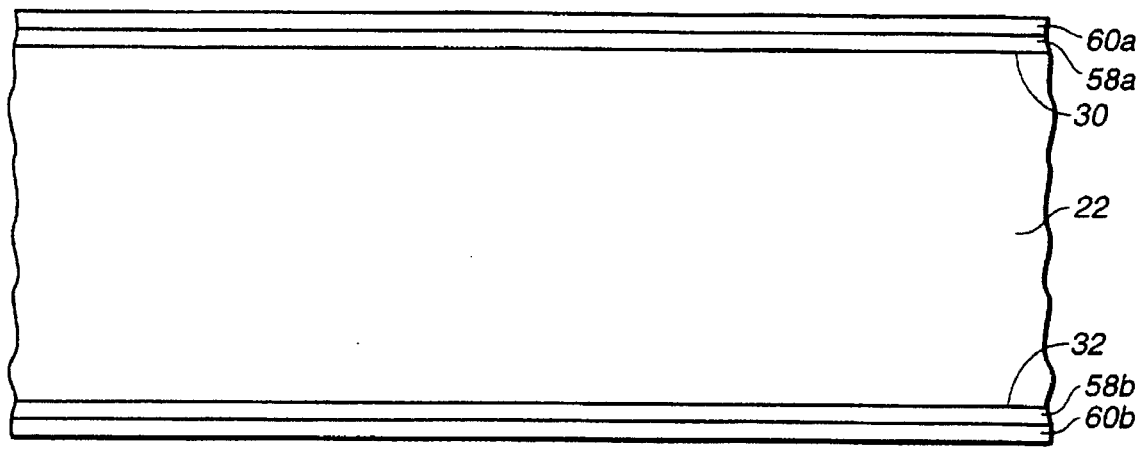
FIG._2A
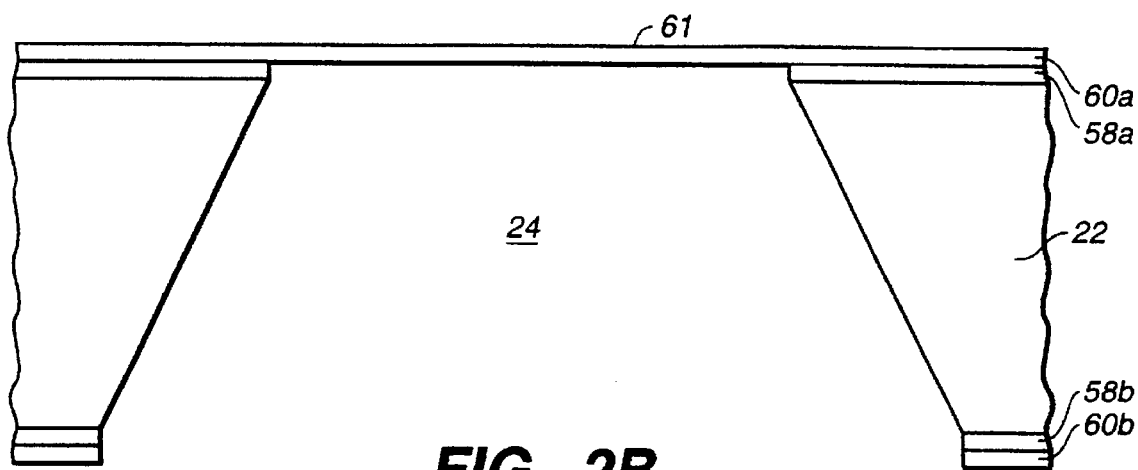
FIG._2B
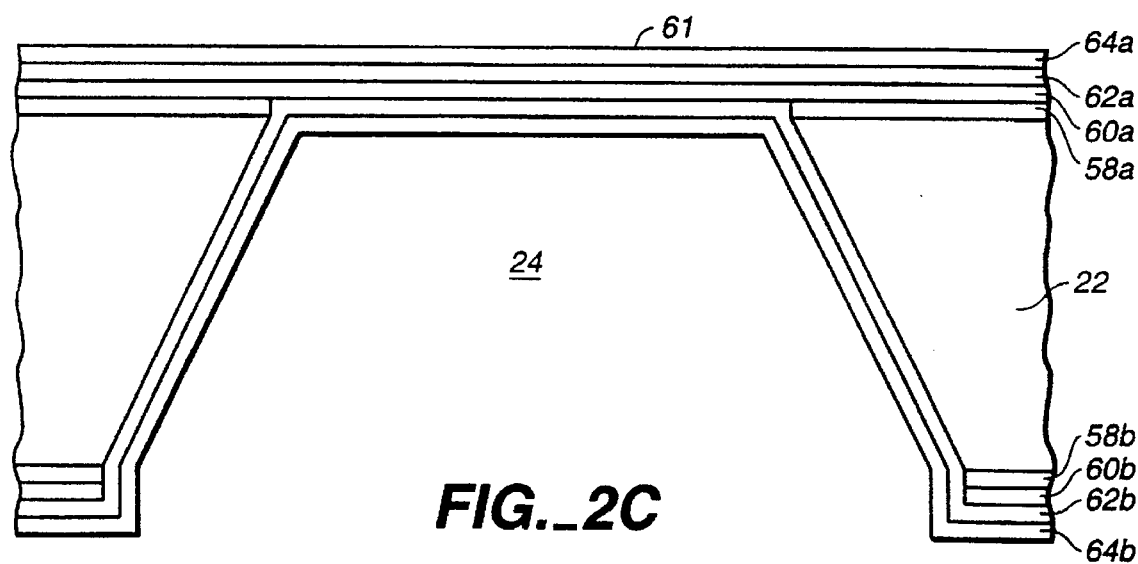
FIG._2C

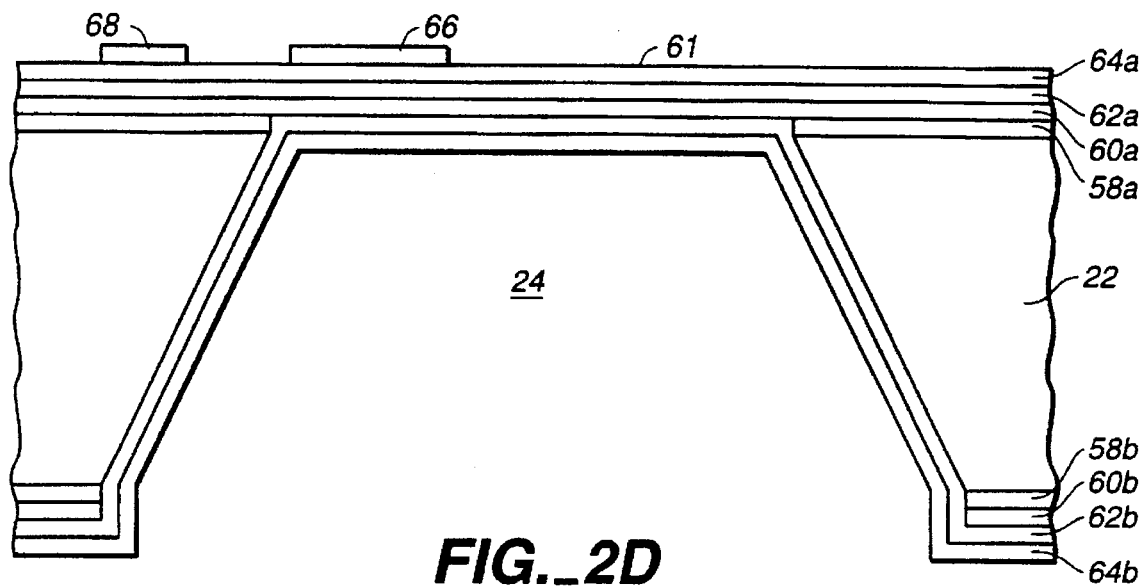
FIG._2D
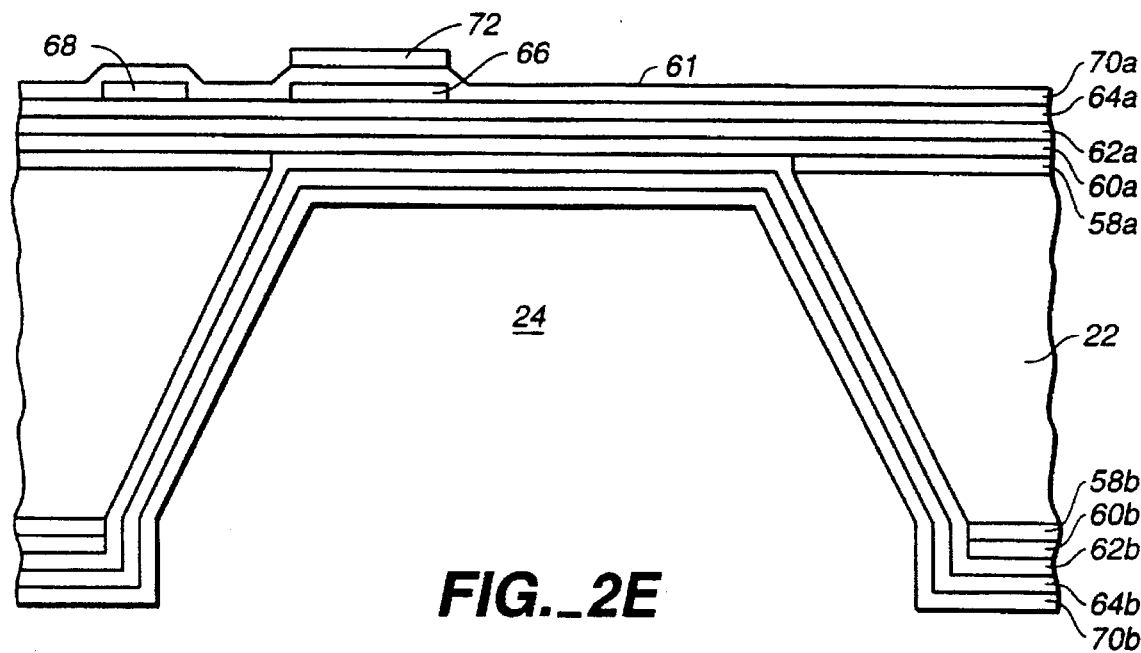
FIG._2E

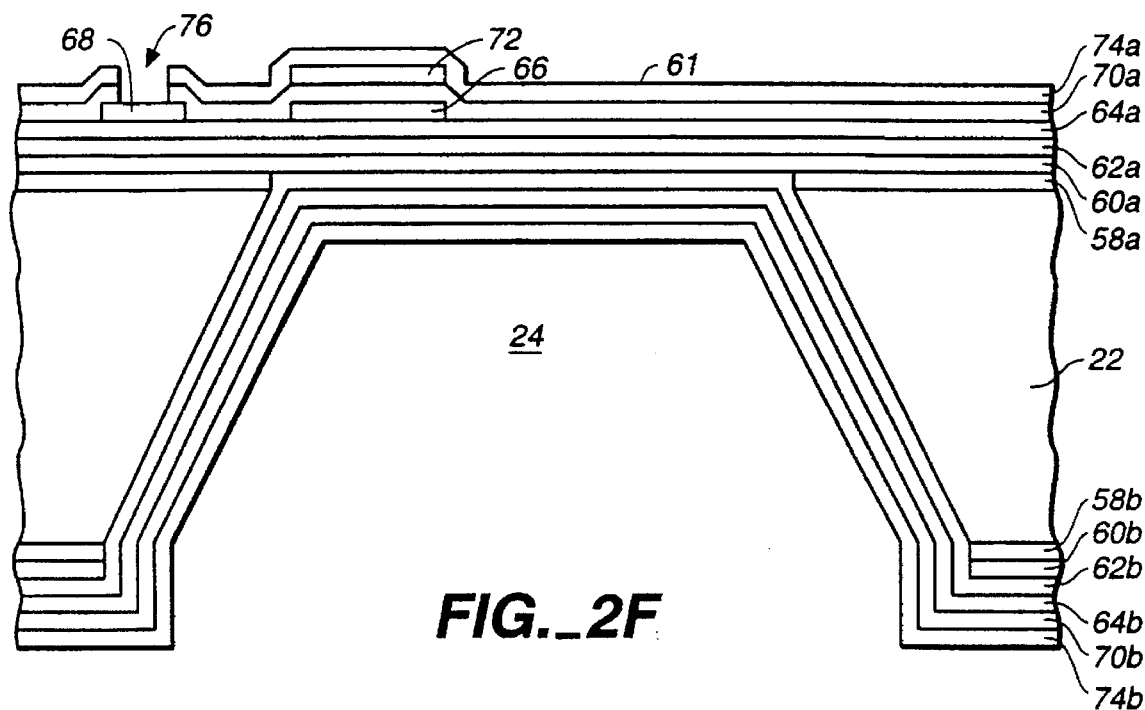
FIG._2F
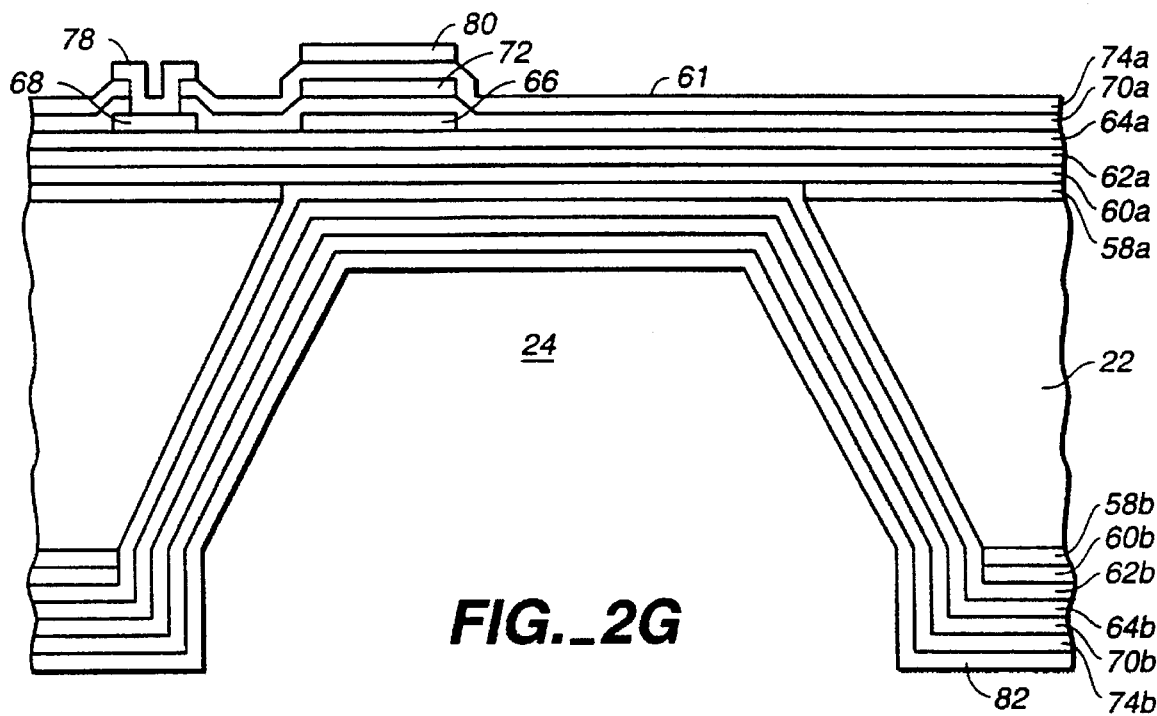
FIG._2G

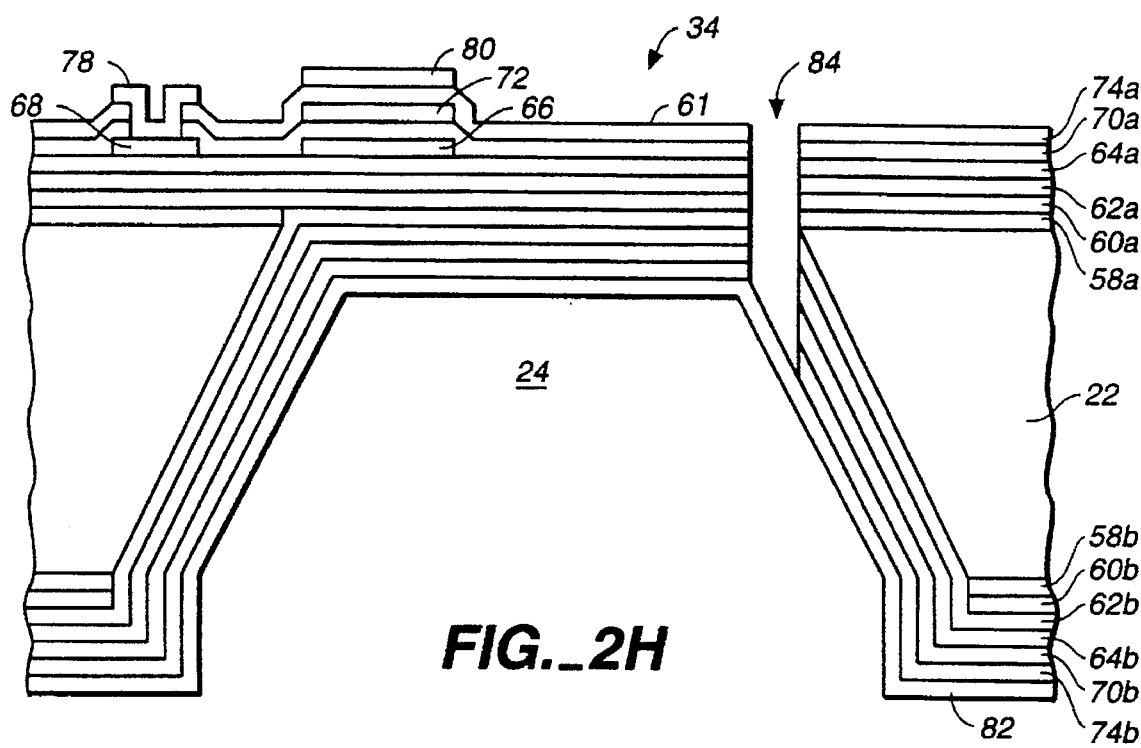
FIG._2H
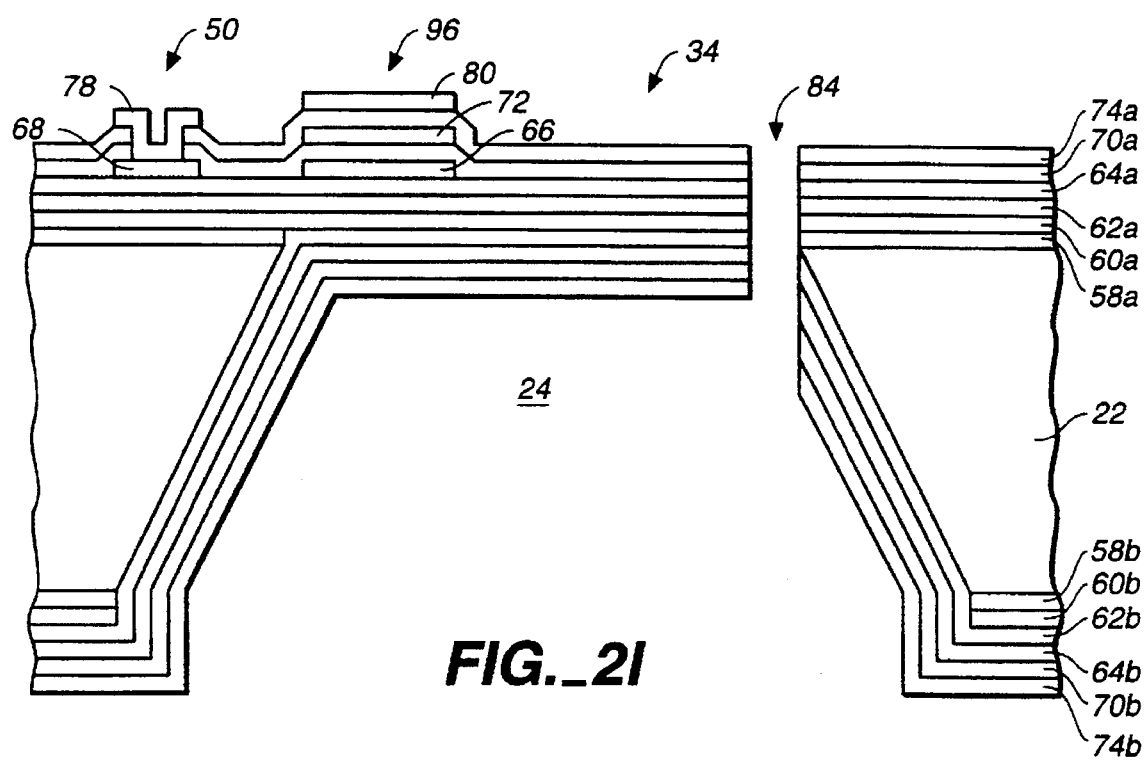
FIG._2I

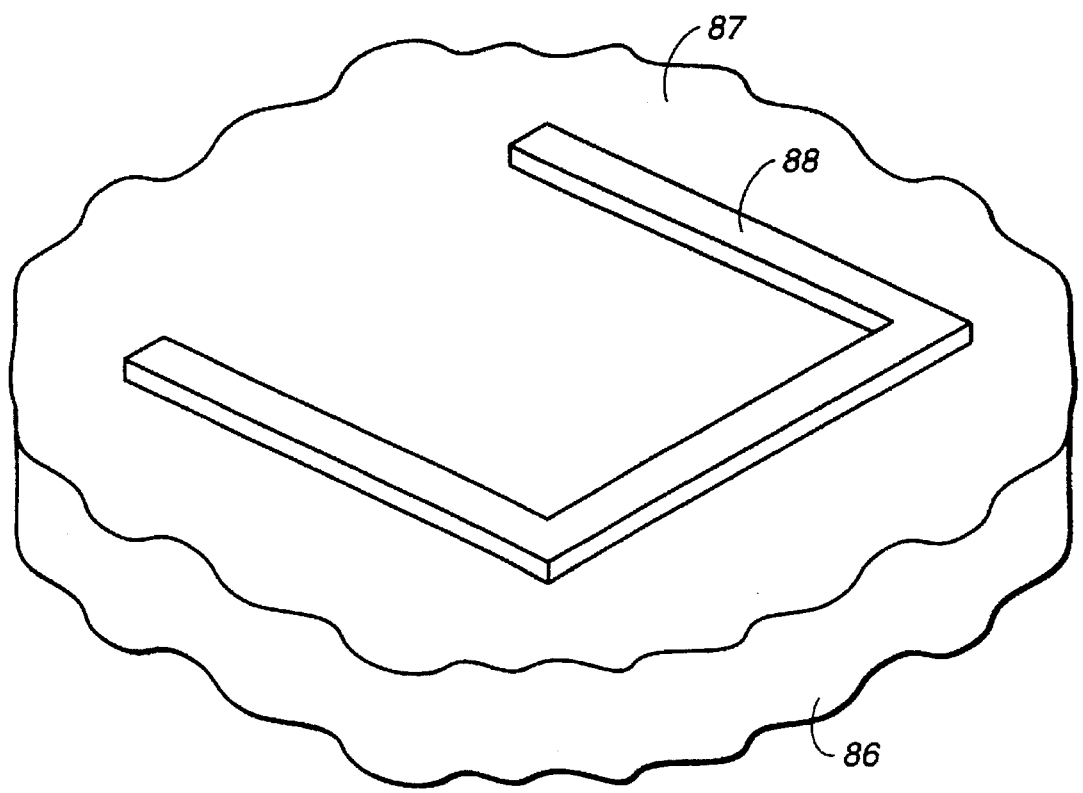
FIG._3B
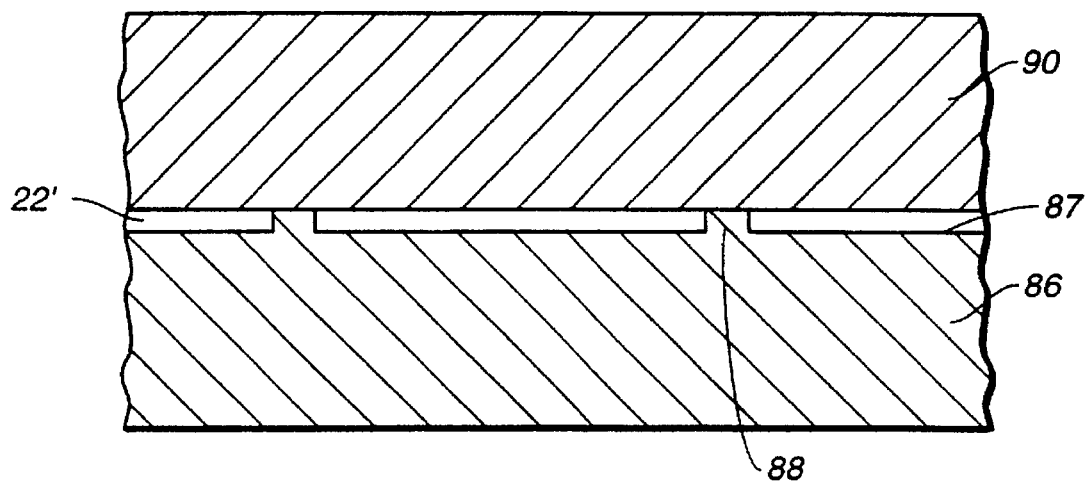
FIG._3C

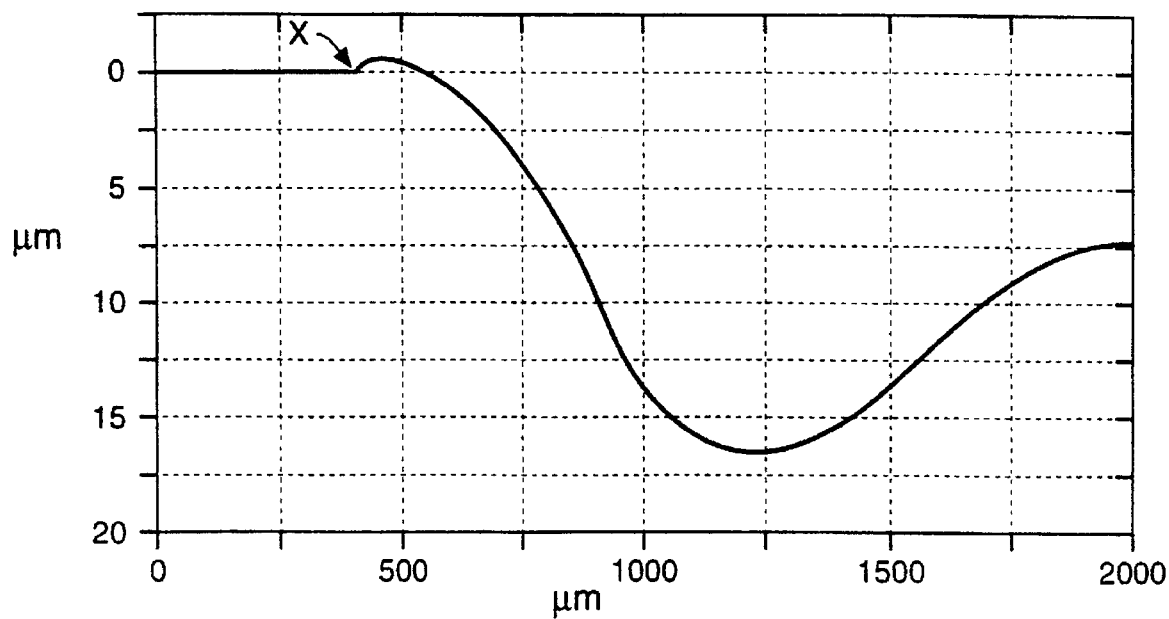
FIG._4
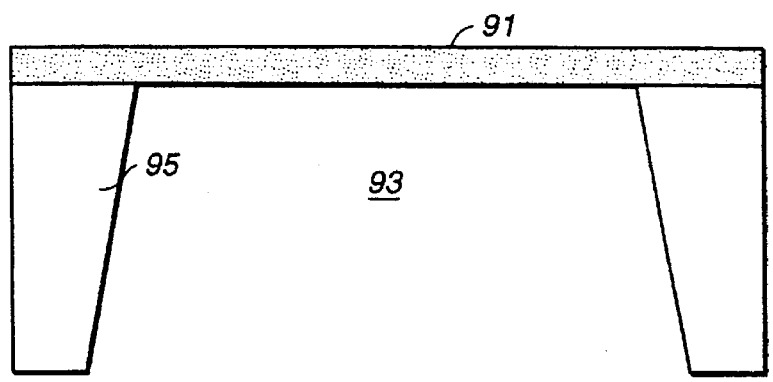
FIG._6A
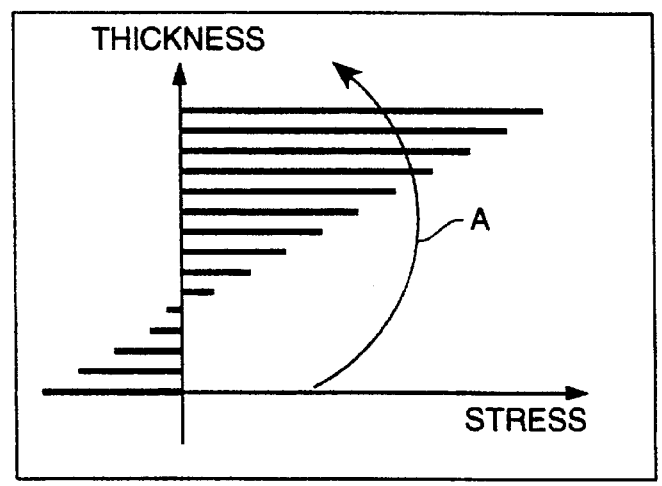
FIG._6B

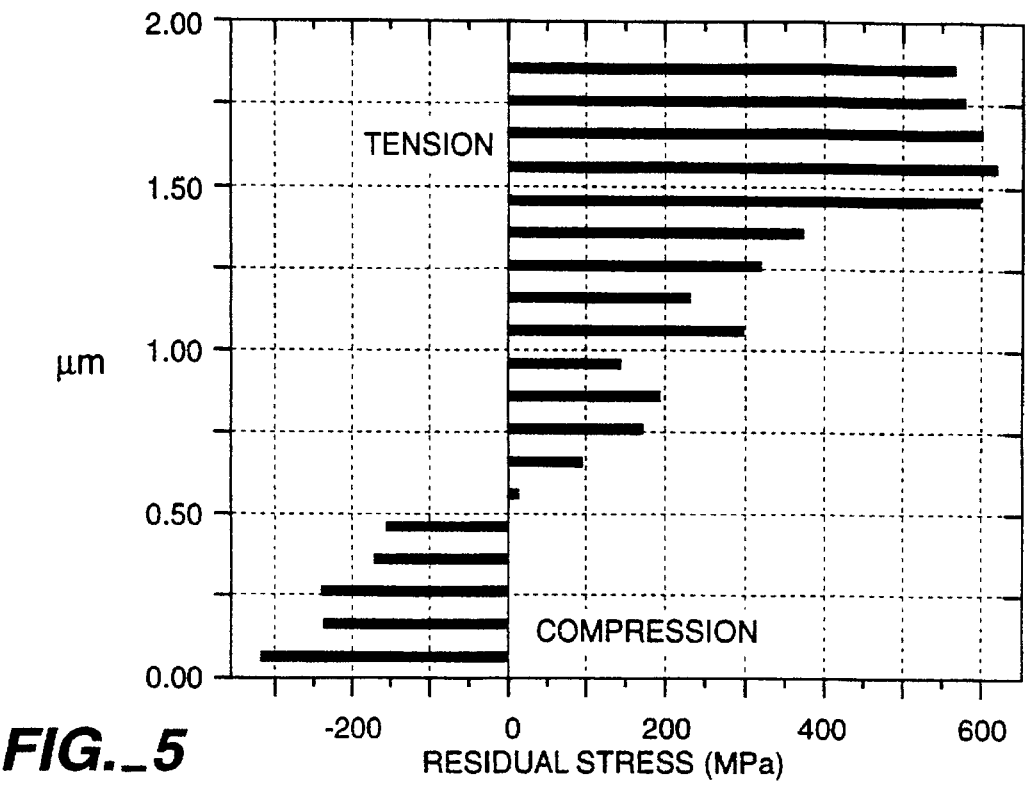
FIG._5
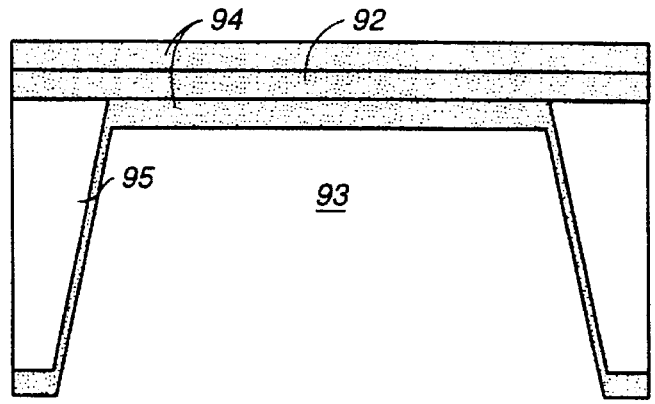
FIG._7A
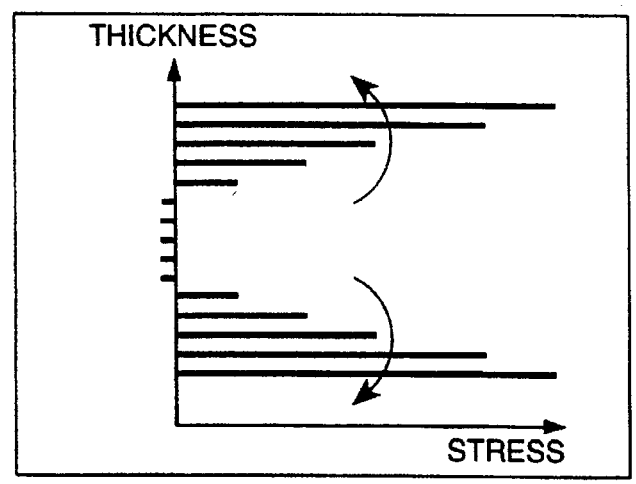
FIG._7B

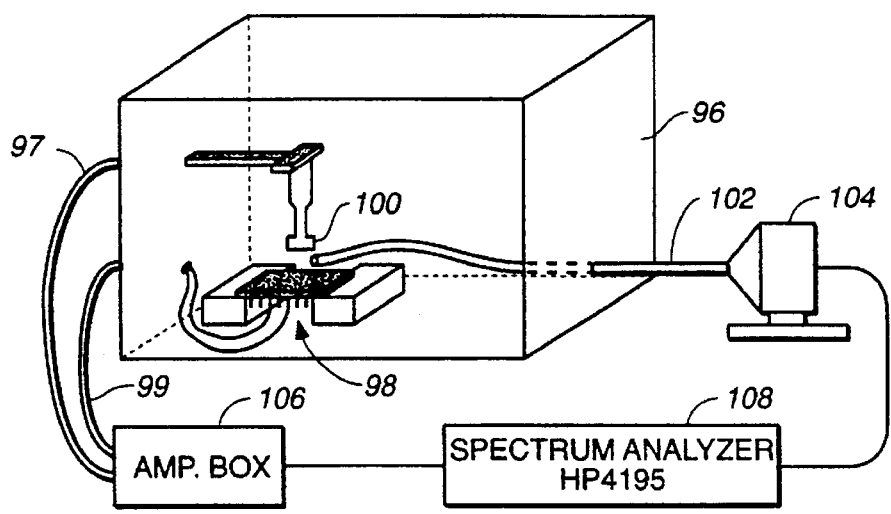
FIG._8
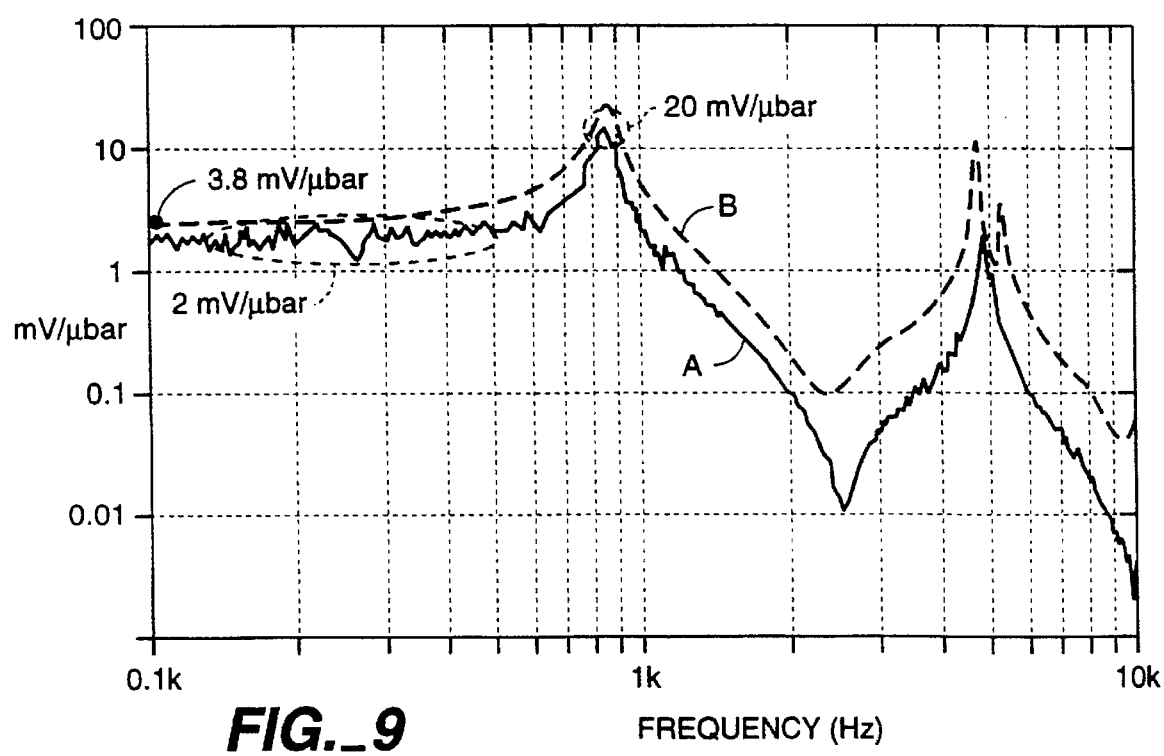
FIG._9 FREQUENCY (Hz)

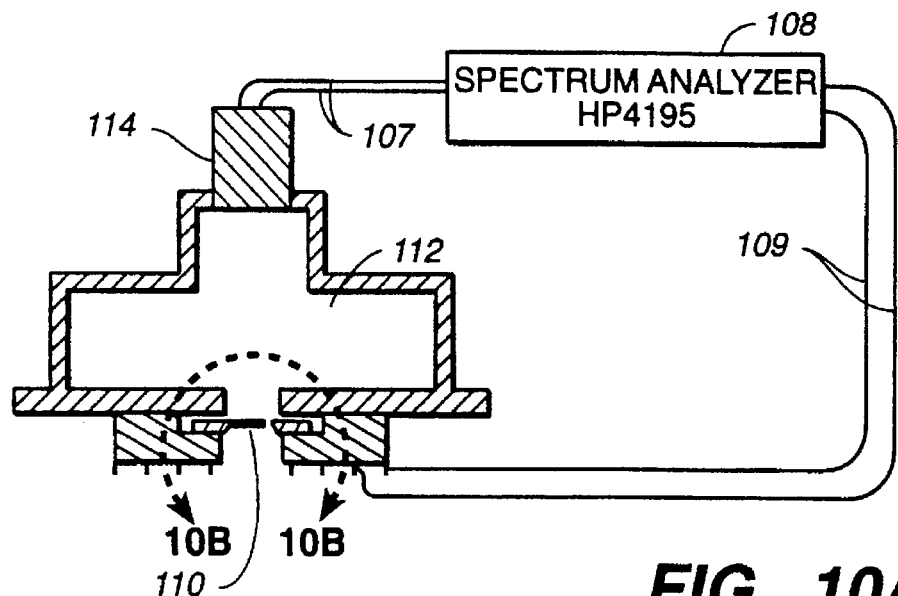
FIG._10A
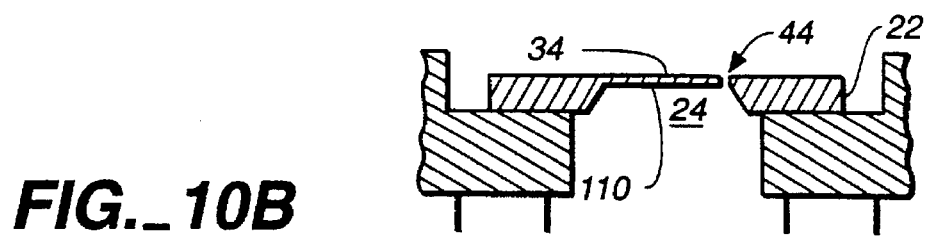
FIG._10B
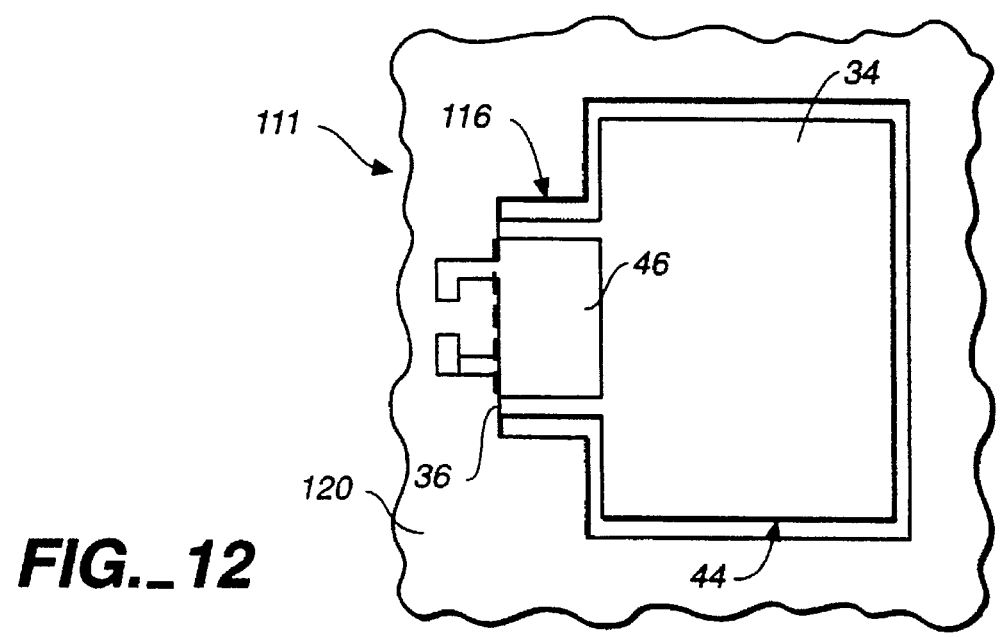
FIG._12

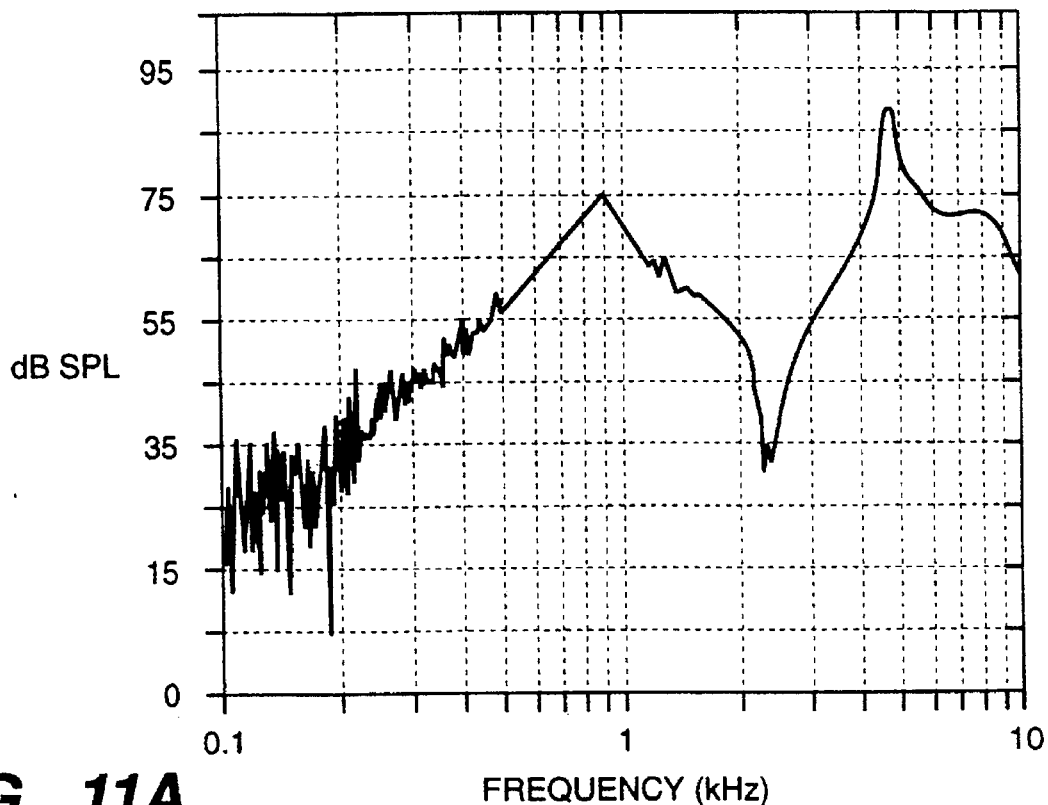
FIG._11A
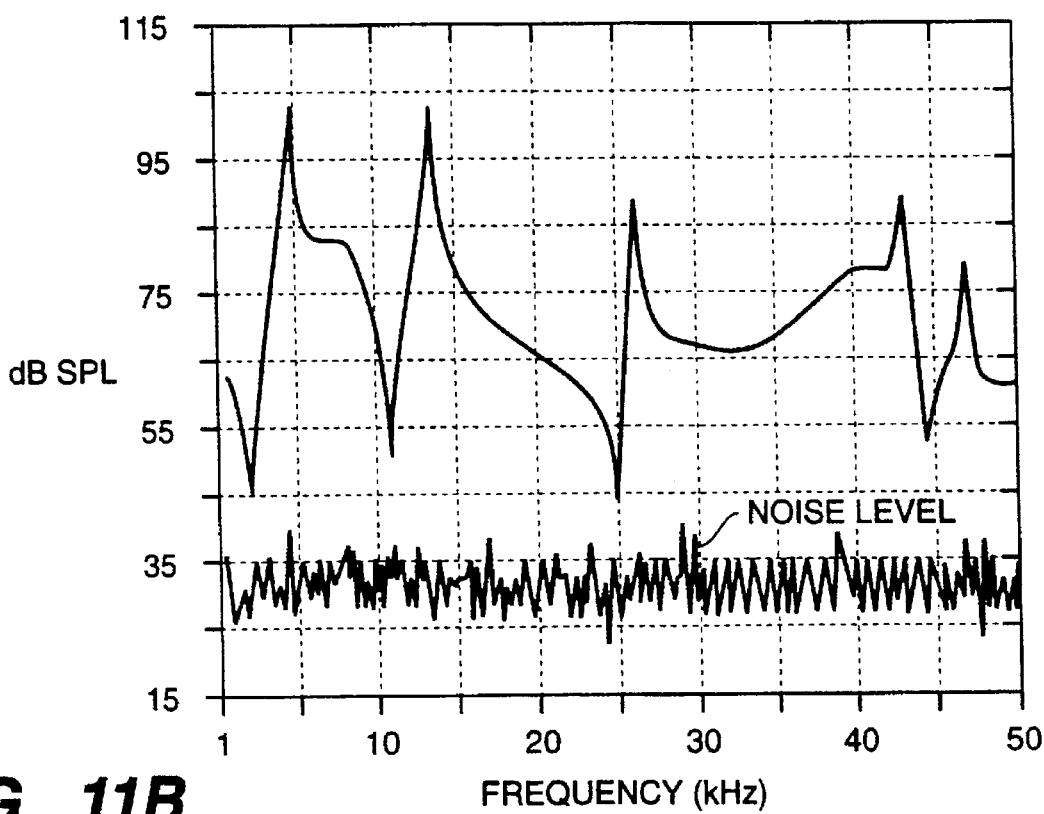
FIG._11B

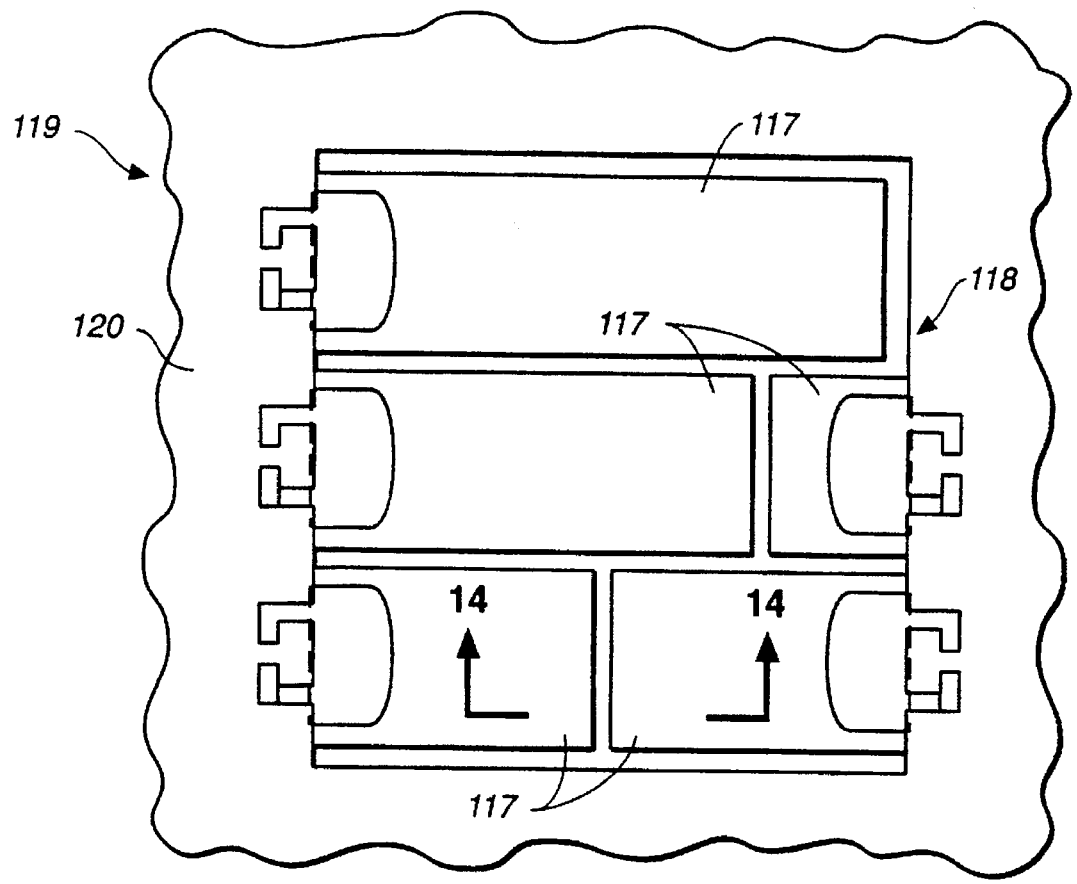
FIG._13
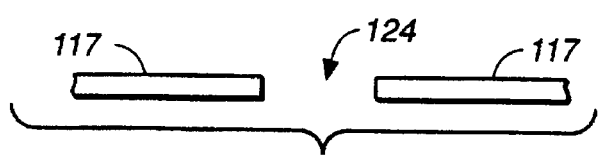
FIG._14A
FIG._14B
FIG._14C

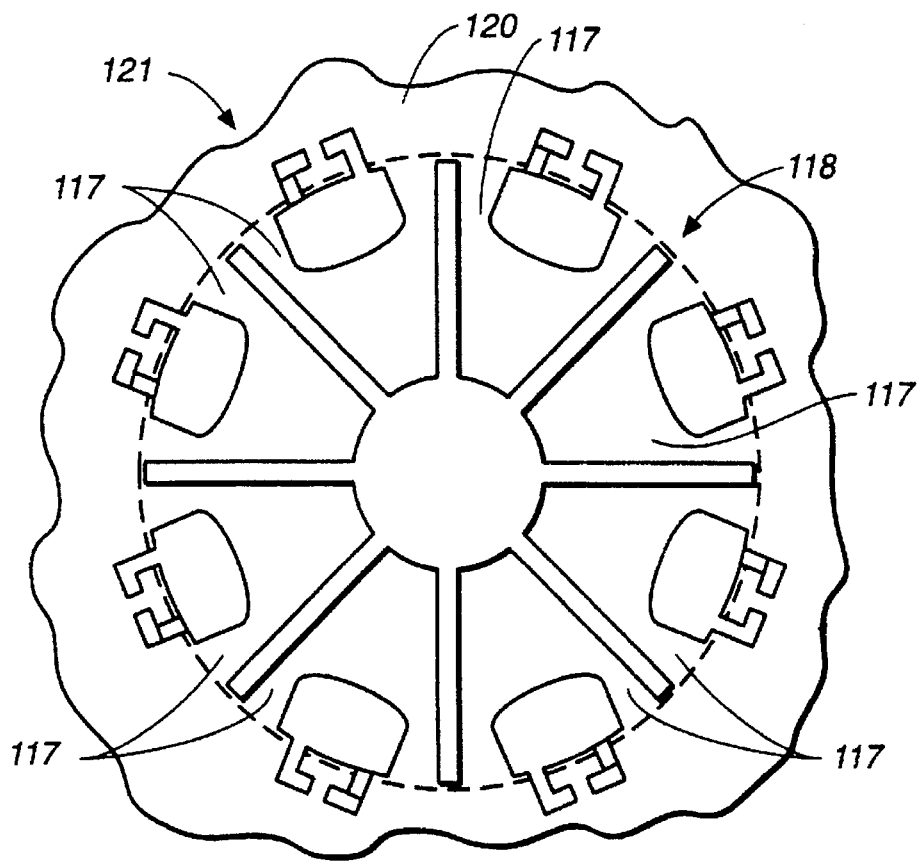
FIG._15
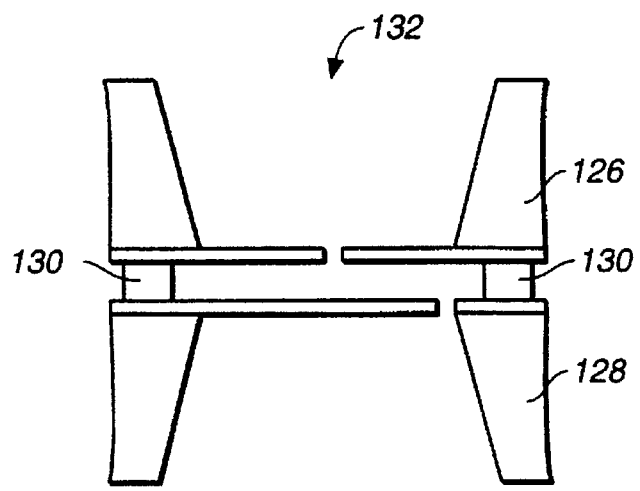
FIG._16

CANTILEVER PRESSURE TRANSDUCER

STATEMENT AS TO RIGHTS

This invention was made with Government support under Grant Nos. ECS-81-20562 and ENG-78-22193 awarded by the National Science Foundation. The Government has certain rights to this invention.

CROSS-REFERENCE TO RELATED APPLICATIONS

This application is a continuation-in-part of U.S. patent application Ser. No. 08/072,294, filed Jun. 4, 1993 now abandoned, the disclosure of which is hereby incorporated by reference.

BACKGROUND OF THE INVENTION

The present invention relates generally to micromachined pressure transducers, and more particularly to a microphone or microspeaker comprising a cantilever structure.

Among the advantages of micromachining of pressure transducers are improved dimensional control, extreme miniaturization, the ability to integrate with on-chip circuitry, and potential low-cost as a result of batch processing.

Acoustic pressure transducers function as microphones or microspeakers. Microphones are pressure sensors that detect airborne sound pressures that are ten orders of magnitude lower than ambient pressure. Hence, a microphone needs an extremely compliant diaphragm to have an acceptable sensitivity. The diaphragm is the member that moves in response to changes in pressure.

The micromachined pressure sensors with piezoelectric readout initially had relatively thick diaphragms (on the order of tens of microns) bulk micromachined from a substrate, such as single-crystal silicon. Control of the thickness and of the latent stress in such diaphragms was inadequate for use at very thin dimensions. When use of very thin, of the order of microns, diaphragms was attempted, the resulting diaphragm was warped.

A novel process for low-stress silicon nitride thin film deposition is disclosed in U.S. Pat. No. 4,783,821, issued Nov. 8, 1988. This process made possible the fabrication of thin-film diaphragm pressure transducers. The higher compliance of the thin-film diaphragm allowed production of more sensitive microphones. These and the earlier thick diaphragms are clamped on all four edges or all four corners, resulting in a tensioned diaphragm. The tensioning is necessary to control the shape of diaphragms whose residual stresses, together with the stresses of the transducers attached to the diaphragms, tend to warp them, even in the case of the newer low stress silicon nitride films. The tension, however, decreases the compliance of the diaphragm and, as a result, the sensitivity of the microphone.

Cantilever diaphragms are much more compliant than tensioned diaphragms. Use of a cantilever would increase the sensitivity of a microphone and the intensity of the output of a microspeaker. Maximizing the effective device area, minimizing acoustic leakage (reduction of the pressure difference on the two sides of the diaphragm due to air flow around it), and controllability of the device parameters, all require fabrication of substantially flat diaphragms. This has not heretofore been possible with thin-film, cantilever diaphragm and transducer structures. Attempts to fabricate such structures resulted not only in warped diaphragms, but in many cases the residual stresses led to breakage of the diaphragm during the cantilever patterning.

Accordingly, an object of the present invention is to provide a micromachined pressure transducer having a cantilever diaphragm.

Another object of the present invention is to provide a method for fabrication of a substantially flat cantilever diaphragm and transducer with high yield.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to a micromachined device having a cantilever structure covering the majority of an opening in a frame or substrate. When the cantilever structure is in equilibrium, its deflection out of the plane of the opening is less than about 100 μm.

The cantilever structure may include three adjacent sublayers, the middle one designated the second sublayer, and the other two designated first and third. The first and third sublayers have about the same average stress. The magnitude of the difference between the maximum and the minimum stress of the second layer, tensile and compressive stress being given opposite sign, is less than the magnitude of the average stress of the first sublayer.

The method of the present invention includes providing an article comprising a substantially planar first thin film having first and second exposed surfaces. Second and third films are grown on the first and second exposed surfaces of the first thin film. At least one slit is then etched through at least part of the resulting thin film multilayer to define a multilayer thin film cantilever.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

FIG. 1 is a perspective, partial cross-sectional view of a pressure transducer according to the present invention.

FIGS. 2A–2I are cross-sectional views, at several stages of fabrication of the transducer of FIG. 1, along line 2—2 of FIG. 1.

FIG. 3A is a perspective view of a pressure transducer according to another embodiment of the present invention.

FIG. 3B is a perspective view of a patterned silicon wafer used as part of a mold for casting the frame and cantilever of the pressure transducer of FIG. 3A.

FIG. 3C is a cross-sectional view of a mold for casting the frame and cantilever of the pressure transducer of FIG. 3A.

FIG. 4 is a graph of the surface profile of a cantilever structure according to the present invention.

FIG. 5 is a graphical illustration of the residual stress as a function of thickness in a silicon nitride thin film.

FIG. 6A is a cross-sectional view of a silicon nitride thin film membrane grown in one direction with only one surface exposed during the growth.

FIG. 6B is a schematic diagram of the residual stress as a function of thickness of the membrane of FIG. 6A and of the bending tendency of the membrane.

FIG. 7A is a cross-sectional view of a silicon nitride thin film membrane grown according to the present invention.

FIG. 7B is a schematic diagram of the residual stress as a function of thickness of the membrane of FIG. 7A and of the bending tendency of the membrane.

FIG. 8 is schematic diagram of the experimental set-up of the measurement of a microphone according to the present invention.

FIG. 9 is a graph of the sensitivity of a microphone according to the present invention as a function of frequency.

FIGS. 10A is a schematic diagram of the experimental set-up of the measurement of a microspeaker according to the present invention.

FIG. 10B is an exploded view of the cantilever device of FIG. 10A.

FIGS. 11A and 11B are graphs of the response of a microphone according to the present invention as a function of frequency.

FIG. 12 is a plan view of a pressure transducer according to the present invention shaped to increase the compliance of the cantilever diaphragm.

FIGS. 13 and 15 are plan views of pressure transducers according to the present invention comprising several cantilever structures.

FIGS. 14A–14C are cross-sectional views along line 14—14 of FIG. 13 illustrating the possibility of coupling neighboring cantilevers.

FIG. 16 is a schematic cross-sectional view of a sound intensity meter.

DESCRIPTION OF THE PREFERRED EMBODIMENTS

The present invention will be described in terms of a number of preferred embodiments. The preferred embodiments are thin film cantilever pressure transducers and methods for fabrication of such transducers. Such a structure 20 is shown in FIG. 1.

Structure 20 comprises a substrate or frame 22 having a cavity 24. Substrate 22 may be 500–550 microns (μm) thick as indicated by dimension "t". Cavity 24 has openings 26 and 28 at surfaces 30 and 32 of substrate 22, respectively. Opening 26 may be a square having sides 2000 μm long. Covering a majority of opening 26 is a thin film cantilever structure 34 which may be 2–4 μm thick. Cantilever structure 34 has one captive edge 36 and three free edges 38, 40 and 42. A gap 44 surrounds the free edges. Gap 44 may be 10 μm wide. In order to minimize acoustic leakage, it is important to minimize the area of gap 44, such that cantilever structure 34 substantially covers opening 26. A transducer 46 such as a piezoelectric transducer overlaps cantilever structure 34 close to captive edge 36 but without overlapping substrate 22. Transducer 46 may comprise an insulated piezoelectric film sandwiched between two electrode films, one of which is exposed at the top surface of the transducer. For the sake of clarity, the piezoelectric film and two electrode films are not shown. Overlapping substrate 22 are contact 48 for the top transducer electrode and contact 50 for the bottom transducer electrode. Transducer 46 has one edge 53 parallel and very close to the captive edge 36 of cantilever structure 34, two other edges 52 and 54 parallel and close to edges 42 and 38 of the cantilever structure, and one edge 56 which preferably has the shape of a line of constant strain of cantilever structure 34 when subject to a pressure difference at its two surfaces.

The present invention may be practiced using transducers other than piezoelectric. For example, magnetostrictive, piezoresistive or, in the case of microspeakers, thermal transducers could be used.

The fabrication of transducer 20 will be described with reference to FIGS. 2A–2I. It may start using a prime grade, 4-inch <100> crystalline orientation silicon wafer as substrate 22. Silicon dioxide films 58a and 58b, approximately 0.2 μm thick, are thermally grown as shown in FIG. 2A on surfaces 30 and 32 of substrate 22, respectively.

Low stress silicon nitride films 60a and 60b, approximately 0.5 μm thick, are then grown using low pressure chemical vapor deposition (LPCVD). The films are grown for two hours at a temperature of 835° C. in a 300 millitorr (mTorr) ambient of 6:1 ratio dichlorosilane ($SiCl_2H_2$) and ammonia ($NH_3$).

Cavity 24 is fabricated next beginning with patterning of films 58b and 60b and substrate 22. First, the top surface of film 60a is covered with photoresist, which is hard baked without any exposure or developing. The back side of the substrate is next masked with photoresist and openings are patterned in the area to be etched to form cavity 24. Silicon nitride film 60b is plasma etched using a mixture of sulfur hexafluoride ($SF_6$) and helium. Thermal oxide 58b is wet etched in buffered hydrofluoric acid (HF). The photoresist is removed using an oxygen plasma and the silicon dioxide and nitride films are used as a mask during the silicon etching. Substrate 22 is wet etched anisotropically using a solution of Pyrocatechol or Catechol 320 g/Pyrazine 6 g/deionized water 320 milliliters (ml)/Ethylenediamine 1000 ml at 105° C. This solution does not appreciably etch <111> planes of silicon, so that the resulting side walls of cavity 24 are <111> planes and there is very little undercut of films 58b and 60b. The silicon dioxide film 58a exposed by the etching of the substrate is next wet etched using hydrofluoric acid (HF). The resulting structure or article is shown in FIG. 2B. The top opening of cavity 24 is closed by a thin film membrane 61. At this stage in the processing, membrane 61 is made of silicon nitride film 60a, but in subsequent processing steps, as discussed below, additional films will be added to membrane 61, on both sides of film 60a.

Silicon nitride films 62a, 62b and silicon dioxide films 64a, 64b are deposited next using LPCVD. Films 62a, 62b are low stress silicon nitride, approximately 0.5 μm thick. These films are deposited for two hours at 835° C., in a 300 millitorr (mTorr) ambient of 4:1 ratio $SiCl_2H_2$ and $NH_3$. Silicon nitride has been deposited on both sides of membrane 61. Films 64a, 64b are low-temperature oxide (LTO) silicon dioxide, approximately 0.2 μm thick. These films are deposited for 10 minutes (min) at 450° C., in an ambient of 3:5 ratio silane ($SiH_4$) and oxygen. They are then annealed in nitrogen at 950° C. for 20 min. Silicon dioxide has been deposited on both sides of membrane 61. The resulting structure is shown in FIG. 2C.

The lower electrode of transducer 46 is fabricated next, by depositing and patterning a polysilicon film. The polysilicon film is deposited by LPCVD and patterned by plasma etching as well known in the art. For example, an approximately 0.2 μm polysilicon film may be deposited in one hour at 610° C., using 100:1 ratio of $SiH_4$ and phosphine ($PH_3$), followed by annealing in nitrogen at 950° C. for 20 min. Photoresist is then used to mask the area of the lower electrode of transducer 46 (FIG. 1). The backside of the substrate is not masked, such that the polysilicon on the back side is etched completely. The polysilicon may be plasma etched in a mixture of carbon tetrachloride ($CCl_4$), helium and oxygen. After removal of the photoresist, the structure of FIG. 2D is obtained. Transducer bottom electrode 66 overlaps membrane 61 close to its edge but without overlapping substrate 22. Contact lead 68 overlaps substrate 22.

Insulating layers 70a and 70b, shown in FIG. 2E, are next deposited. These layers are approximately 0.2 µm thick LPCVD silicon dioxide deposited in one hour at 450° C., using 60:100:10.3 $SiH_4/O_2/PH_3$. They are then annealed in nitrogen at 950° C. for 20 min. Again, both sides of membrane 61 are coated.

A piezoelectric zinc oxide (ZnO) film is then deposited and patterned. The film is grown by RF-magnetron sputtering onto a substrate heated to 200°–300° C., using a 1:1 mixture of argon and oxygen at a pressure of 10 mTorr, to a thickness of approximately 0.5 µm. No film is deposited on the back side. The film is patterned to form a pad 72 overlapping the polysilicon electrode 66, by photolithography without photoresist hard bake and wet etching using a 1:1:20 solution of acetic acid ($CH_3COOH$)/sulfuric acid ($H_2SO_4$)/$H_2O$. The photoresist is then removed using acetone, methanol and water for 30 minutes in each successively. The resulting structure is shown in FIG. 2E.

A third layer of LPCVD silicon dioxide, approximately 0.3 µm thick is then deposited to encapsulate ZnO pad 72. As a result, films 74a and 74b are deposited on the front and back of membrane 61, respectively. The films are grown for 15 min at 450° C., in an ambient of 60:100:0.4 $SiH_4/O_2/PH_3$.

Contact holes for contact to lead 68 are then etched through layers 74a and 70a. The holes are patterned with photolithography and the back side of the wafer is coated with photoresist to protect oxide films 64b, 70b and 74b. Holes 76 are then etched using buffered hydrofluoric acid. After photoresist removal, the structure of FIG. 2F is obtained.

An aluminum film is next grown on the front side of the wafer for contact pad 78 and electrode 80. The film is sputtered to a thickness of approximately 0.8 µm, patterned by photolithography and wet etched as well known in the art, using a potassium ferrocyanide ($K_3Fe(CN)_6$)/potassium hydroxide (KOH) solution. A sacrificial backing aluminum film 82 is then sputtered on the back side to a thickness of approximately 0.5 µm. This film must be less than 1.5 µm thick to avoid breaking membrane 61 with its residual stress, but must be thick enough not to break when membrane 61 is etched as described below. The resulting structure is shown in FIG. 2G.

The shape of cantilever 44 is next defined by etching gap 44 (FIG. 1). After photolithography on the front side, membrane 61 is etched down to the sacrificial backing aluminum layer 82. Wet etching is used for the silicon dioxide layers, and plasma etching for the polysilicon and silicon nitride layers as described above, resulting in the structure of FIG. 2H. Aluminum layer 82 increases the yield by preventing breakage of membrane 61 during this etching step.

Finally, sacrificial backing layer 82 is removed by wet etching after masking the front side to protect electrode 80 and contact pad 78. After removing the photoresist, the structure of FIGS. 1 and 2I is obtained.

The wafer may then be diced with a diamond saw, and individual pressure transducers glued and wire-bonded to ceramic packages which have a 3 millimeter (mm)-diameter ventilation hole formed by a diamond drill. The ventilation hole may be left open during testing or sealed to form a 15 $mm^3$ back-cavity volume. The ventilation hole may be sealed by gluing a suitable backing over the hole on the underside of the ceramic package.

FIG. 3A shows another pressure transducer 20' according to the present invention. This transducer is a polymeric cantilever structure with a thickness of a few to tens of microns. Device 20' comprises a frame 22', a cantilever structure 34' and a transducer 46'. Cantilever structure 34' is separated from frame 22' by a gap 44' over part of the perimeter of structure 34', and is attached to frame 22' over the rest of its perimeter. Overlapping cantilever structure 34' near the portion of its perimeter attached to frame 22' is transducer 46'. Transducer 46' may comprise a piezoelectric layer 72' sandwiched between a lower electrode 66' and an upper electrode 80', having leads 50' and 48', respectively.

With a suitable choice of materials, pressure transducer 20' may be made thin and flexible. Electrodes 66' and 80' and leads 50' and 48' may be thin metal films, and frame 22', cantilever structure 34' and piezoelectric layer 72' may be formed of polymeric materials. For example, frame 22' and cantilever structure 34' may be formed of a structure polymer such as polycarbonate, polystyrene or polyimide. The piezoelectric layer may be PvDF (polyvinylidene difluoride) and TrFE (trifluoroethylene). Such a polymeric pressure transducer may be made integral with other polymer-based objects such as credit cards and smart cards.

Frame 22' and cantilever structure 34' may be cast at the same time using a reusable micromachined mold that may be advantageously made by etching a silicon wafer 86 (FIG. 3B) to form features 88 raised above surface 87 from a few to tens of microns. Features 88 have the shape of the gap 44' to be formed in the resulting polymer structure. Before casting, the surface 87 of mold wafer 86 may be coated with a mold release agent such as a silating agent with fluorocarbon backbone, assuming the mold is made of silicon. Mold wafer 86 may then be coated with a structure polymer precursor, after which a second, flat wafer 90 is put on top of wafer 86. FIG. 3C is a cross-sectional view of the resulting assembly. This arrangement limits the thickness of the structural polymer coating so that it does not overflow features 88.

After polymerization which may be accomplished using a variety of well-known methods, wafer 90 may be removed but frame and cantilever structure 22' and 34' should be left in place on wafer 86 for ease of handling during subsequent processing steps.

Transducer 46' is fabricated next. Lower electrode 66' may be evaporated through a shadow mask. The piezo polymer layer 72' may then be applied by spinning on while an aperture mask is in place over the underlying structure. Upper electrode 80' is then applied, also by evaporation through a shadow mask. Piezoelectric layer 72' may then be poled by applying a voltage between electrodes 66' and 80' during which time the piezoelectric layer is heated and then allowed to return to room temperature.

The advantages of the process described above with reference to FIGS. 2A–2I will be discussed next. It is desired that the resulting cantilever structures 34 (FIG. 1) have out-of-plane deflections less than 100 µm at equilibrium (i.e., when not acted upon by external forces), preferably less than 50 µm and more preferably significantly less than 50 µm. FIG. 4 shows the profile of the highest-deflection section of an actually fabricated cantilever structure, such as structure 34 of FIG. 1, as measured by a profilometer. The vertical axis indicates deflection in microns, and the horizontal axis indicates the position along the cantilever in microns, the captive edge of the cantilever being at a position "x" of approximately 400 µm from the origin. As can be seen, the out-of-plane deflection of the transducer is less than 20 μm. By means of non-contact optical measurements, it has been verified that the profile of FIG. 4 is accurate to within experimental error of 3 μm. Across a given wafer, the majority of the transducers of the present invention have out-of-plane deflections below 35 μm.

Cantilever structures fabricated with the entire silicon nitride deposition as a single layer before the substrate etching were significantly curled upward or downward. As discussed above, this is undesirable because it decreases the effective device area upon which the sound wave impinges in the case of a microphone, or which launches the sound wave in the case of a microspeaker. Additional reasons why a curled cantilever structures are undesirable are an increase in acoustic leakage and possible lack of controllability of the device characteristics.

The downward curl is due to the high residual compressive stress of the ZnO layer of the piezoelectric transducer. It was found that the curl is considerably reduced by patterning the ZnO, such as layer 72 of transducer 46 (FIG. 2I), so that it does not overlap the silicon frame.

The upward curl of the single silicon nitride layer cantilever structures arises because of the gradient of residual stress of the silicon nitride, which is illustrated in FIG. 5 for a typical film deposited as a single layer onto a bulk substrate, such as film 91 of FIG. 6A. The stress profile of FIG. 5 has been obtained by successively removing thin layers of such a film and measuring wafer curvature. In FIG. 5, the vertical axis indicates position along the thickness of a film and the horizontal axis indicates residual stress in megaPascal (MPa), positive for tensile stress and negative for compressive stress. The stress distribution in the silicon nitride seems to be related to annealing during the deposition at 835° C. The earlier a layer is deposited, the longer this layer is annealed. The gradient in the residual stress of a film grown onto a surface of a bulk substrate in only one direction, such as silicon nitride film 91 in FIG. 6A, generates a moment that causes the upward curl, indicated by arrow A in FIG. 6B where the vertical axis indicates position along the thickness of film 91 and the horizontal axis indicates residual stress. Cavity 93 of FIG. 6A was etched, after the growth of film 91, in substrate 95.

FIG. 7A shows the solution used in the process flow of FIGS. 2A–2I in order to produce a cantilever with a symmetric stress distribution in the silicon nitride. It should be noted that the stress distribution in the finished diaphragm, with outer silicon dioxide layers, will also be symmetric for the reasons given below. The initial approximately 0.5-μm-thick silicon nitride layer 92, corresponding to layer 60a in FIG. 2I, is deposited with a 6:1 reactant gas ratio to form the diaphragm prior to bulk micromachining. The low (50 MPa) residual tensile stress of the thin, initial diaphragm makes it more resistant to rupture.

After bulk micromachining, the second approximately 0.5-μm-thick low-stress silicon nitride 94, corresponding to layers 62a and 62b in FIG. 2I, is deposited with a 4:1 reactant gas ratio. The larger tensile stress (250 MPa) of the second layer is used to maintain diaphragm flatness during subsequent processing steps. Since the second silicon nitride deposition occurs on both sides of the original diaphragm, the stress gradients become symmetric as shown in FIG. 7B. The first silicon nitride layer is also annealed during the second layer deposition and its stress distribution becomes negligible. The result is a relatively flat cantilever. This technique of producing a flat cantilever despite the stress gradient in the component films may have applications to other micromachined structures.

The microphone frequency response of the structure of FIG. 1 has been measured using the arrangement of FIG. 8. The measurement was made in an electrically shielded anechoic chamber 96 containing a calibrated reference microphone 100. The test (cantilever diaphragm) microphone 98 of the present invention (whose structure 20 is shown in FIG. 1), and reference microphone 100, respectively, were placed at the same distance from the source of acoustic signals, which was at the end of a 6.5 mm diameter tube 102 that leads into the chamber from an external conventional loudspeaker 104 driven by spectrum analyzer 108. The output signals of test microphone 98 and reference microphone 100 were applied, using lead pairs 99 and 97, respectively, to the input of a high input impedance amplifier 106 connected to spectrum analyzer 108.

FIG. 9 shows the typical measured microphone sensitivity (curve A) when tested without the above-described ceramic package hole backing. The vertical axis indicates sensitivity in mV/μbar (millivolts per microbar, 1 bar=$10^5$ Pa) and the horizontal axis indicates the frequency. The microphone sensitivity is fairly constant at 2 mV/μbar in the low frequency range and rises to 20 mV/μbar at the lowest resonant frequency of 890 Hz. The 2 mV/μbar is the highest reported for a microphone with a micromachined diaphragm. The low-frequency sensitivity and the resonant frequencies are in good agreement with a simulation result given by curve B. Independent testing showed that backing with a 15 $mm^3$ cavity reduces the low-frequency sensitivity by about 8 decibels (dB), to around 0.8 mV/μbar. The simulation result was obtained using a combination of finite-element simulations and analytical modeling.

The microspeaker frequency response of the structure of FIG. 1 has been measured using the arrangement of FIGS. 10A and 10B. The acoustic output of the cantilever device 110 of the present invention (whose structure 20 is shown in FIG. 1), driven by spectrum analyzer 108 through leads 109, was measured using a 2 $cm^3$ coupler 112 with a calibrated microphone 114 connected to spectrum analyzer 108 with leads 107. FIG. 11A shows the microspeaker output in the 100 Hz to 10 kHz frequency range with 4 V (zero-peak) input drive. FIG. 11B shows the sound pressure level produced by the microspeaker in the 1 kHz to 50 kHz frequency range. In FIGS. 11A and 11B, the vertical axis is sound pressure level in dB SPL (decibels sound pressure level) and the horizontal axis is frequency. The resonant frequencies coincide with those of the microphone response at 890 Hz and 4.8 kHz, as expected. The highest output pressure corresponds to approximately 100 dB SPL.

As shown in FIG. 12, which is a plan view of a cantilever pressure transducer 111 of the present invention, the compliance of the diaphragm may be further increased by reducing the length of the diaphragm perimeter where the diaphragm is attached to the frame 120 and providing a narrower portion 116 carrying transducer 46 near the captive edge of diaphragm 34, where most of the diaphragm bending takes place. Transducer 111 may be fabricated using either the method of FIGS. 2A–2I or of FIGS. 3A–3C.

FIGS. 13 and 15 are plan views of cantilever pressure transducers 119 and 121, according to the present invention, respectively. Transducers 119 and 121 may be fabricated using either the method of FIGS. 2A–2I or of FIGS. 3A–3C. Transducers 119 and 121 have a plurality of cantilever structures 117 sharing an opening 118 in a frame 120. Transducer 119 has five cantilever structures 117, and transducer 121 has eight cantilever structures 117. In FIG. 15, the opening is substantially circular and the cantilever structures are positioned substantially radially over the opening. As shown in FIG. 14A, the cantilever structures may be free and separated by gaps 124, or, as shown in FIGS. 14B and 14C, the cantilever structures may be coupled by thinner (120, FIG. 14B) or corrugated (122, FIG. 14C) diaphragms. These options provide additional flexibility in the design of pressure transducers allowing control over the details of their frequency response.

FIG. 16 shows how two cantilever pressure transducers 126 and 128 can be stacked to form a sound intensity meter 132. As is well known, the upper limit of the frequency range over which the intensity meter is functional is increased by locating the pressure transducers closer to each other. Pressure transducers 126 and 128 may be located at a short distance relative to each other using spacers 130.

In summary, micromachined cantilever pressure transducers, such as microphones and microspeakers, and methods for their fabrication have been described. By controlling the distribution of residual stress, 2000 µm long cantilevers were fabricated whose maximum out-of-plane deflections were typically no more than 35 µm. The microspeaker output is proportional to the input drive, and rises to approximately 100 dB SPL at 4.8 kHz and 6 V (zero-peak) drive. The microphone sensitivity is fairly constant at 2 mV/µbar in the low frequency range, and is 20 mV/µbar at the lowest resonant frequency of 890 Hz. The high microphone sensitivity and the high microspeaker output are due to the high compliance of the cantilever diaphragm.

The present invention has been described in terms of a preferred embodiment. The invention, however, is not limited to the embodiment depicted and described. Rather, the scope of the invention is defined by the appended claims.

What is claimed is:

1. A micromechanical device comprising:
   a frame having an opening;
   at least one cantilever structure attached to said frame over a portion of a perimeter of said opening and covering a majority of said opening; and
   said cantilever structure including three adjacent sublayers designated first, second and third such that said second sublayer is adjacent to said first and third sublayers, said first and third sublayers formed of substantially the same first material and having about the same average stress, and said second layer formed of a second material and having a minimum stress and a maximum stress, the difference between said maximum stress and said minimum stress being less than the magnitude of the average stress of said first sublayer.

2. The device of claim 1 wherein, when said cantilever structure is in equilibrium, its deflection out of the plane of said opening is less than about 50 µm.

3. The device of claim 2 wherein said cantilever structure includes silicon nitride.

4. The device of claim 1 further including a transducer, said transducer overlapping said cantilever structure and not overlapping said substrate.

5. The device of claim 4 wherein said transducer is from the group consisting of piezoelectric, piezoresistive, capacitive, magnetostrictive and thermal transducers.

6. The device of claim 4 wherein said transducer includes a zinc oxide thin film.

7. The device of claim 1 wherein said first and third sublayers have opposite stress gradients.

8. The device of claim 7 further including a transducer, said transducer overlapping said cantilever structure and not overlapping said substrate.

9. The device of claim 8 wherein said transducer is from the group consisting of piezoelectric, piezoresistive, capacitive, magnetostrictive and thermal transducers.

10. The device of claim 8 wherein said transducer includes a zinc oxide thin film.

11. The device of claim 1 wherein an average stress of said second sublayer is less than the average stress of said first layer.

12. The device of claim 1 wherein said first and second materials include silicon.

13. The device of claim 1 wherein said first and second material include silicon nitride.

14. A micromechanical device, comprising:
   a substrate having first and second surfaces, and a cavity with an opening at said first surface;
   at least one multilayer cantilever structure attached to said first surface of said substrate over a portion of a perimeter of said opening and covering a majority of said opening; and
   wherein said cantilever structure includes three adjacent sublayers designated first, second and third such that said second sublayer is adjacent to said first and third sublayers, said first and third sublayers having about the same average stress, said second sublayer having a maximum stress and a minimum stress, compressive and tensile stresses considered to have opposite sign, and the magnitude of the difference between said maximum stress and said minimum stress being less than the magnitude of the average stress of said first sublayer, said first, second and third sublayers including silicon nitride.

15. A micromechanical device comprising:
   a substrate having first and second surfaces, and a cavity with an opening at said first surface;
   at least one multilayer cantilever structure attached to said first surface of said substrate over a portion of a perimeter of said opening and covering a majority of said opening; and
   wherein said cantilever structure includes three adjacent sublayers designated first, second and third such that said second sublayer is adjacent to said first and third sublayers, said first and third sublayers having about the same average stress, said second sublayer having a maximum stress and a minimum stress, compressive and tensile stresses considered to have opposite sign, the magnitude of the difference between said maximum stress and said minimum stress being less than the magnitude of the average stress of said first sublayer, and said first and third sublayers having opposite stress gradients, said first, second and third sublayers including silicon nitride.

16. A micromechanical device, comprising:
   a substrate having first and second surfaces, and a cavity with an opening at said first surface;
   at least one multilayer cantilever structure attached to said first surface of said substrate over a portion of a perimeter of said opening and covering a majority of said opening; and
   wherein said cantilever structure includes three adjacent sublayers designated first, second and third such that said second sublayer is adjacent to said first and third sublayers, said first and third sublayers having about the same average stress, said second sublayer having a maximum stress and a minimum stress, compressive and tensile stresses considered to have opposite sign, the magnitude of the difference between said maximum stress and minimum stress being less than the magnitude of the average stress of said first sublayer, and an average stress of said second sublayer is less than the average stress of said first sublayer, said first, second and third sublayers including silicon nitride.

17. A method for fabrication of a polymeric cantilever structure, comprising:

providing a first mold element having features raised above a first flat surface;

coating said first surface with a polymer precursor;

placing a second mold element with a second flat surface parallel to the first surface and in contact with the raised features; and polymerizing said polymer precursor.

18. A method for fabrication of a thin film cantilever structure, comprising:

providing an article comprising a substantially planar first thin film, said thin film having first and second exposed surfaces;

growing second and third thin films on said first and second surfaces, respectively, to form a thin film multilayer; and etching at least one slit through at least part of the thin film multilayer to define at least one multilayer thin film cantilever.

19. The method of claim 18 further including:

growing a sacrificial backing layer before etching said slit; and etching said sacrificial backing layer after etching said slit; and wherein said sacrificial backing layer is not etched when said slit is etched.

20. The method of claim 18 wherein said second and third films are grown at the same time.

21. The method of claim 20 wherein said second and third films are grown using chemical vapor deposition.

22. The method of claim 21 wherein said second and third films include silicon nitride.

23. The method of claim 18 wherein said first film includes silicon nitride grown on a silicon dioxide-coated substrate by chemical vapor deposition in an atmosphere with a ratio of silicon atomic content to nitrogen atomic content of about 6:1.

24. The method of claim 18 further including a step of growing fourth and fifth thin films on said second and third thin films, respectively before the etching of said slit.

25. The method of claim 24 further including:

growing a sacrificial backing layer before etching said slit; and etching said sacrificial backing layer after etching said slit; and wherein said sacrificial backing layer is not etched when said slit is etched.

26. The method of claim 24 wherein said fourth and fifth films are grown at the same time.

27. The method of claim 26 wherein said fourth and fifth films are grown using chemical vapor deposition.

28. The method of claim 27 wherein said fourth and fifth films include silicon dioxide.

29. The device of claim 2 wherein said frame and said cantilever structure include a polymeric material.

* * * * *